United States Patent [19]
Yoon

[11] Patent Number: 5,575,804
[45] Date of Patent: * Nov. 19, 1996

[54] SAFETY PENETRATING INSTRUMENT WITH CANNULA MOVING DURING PENETRATION AND TRIGGERED SAFETY MEMBER PROTRUSION

[76] Inventor: InBae Yoon, 2101 Highland Ridge Dr., Phoenix, Md. 21131

[*] Notice: The term of this patent shall not extend beyond the expiration date of Pat. No. 5,431,635.

[21] Appl. No.: 300,535

[22] Filed: Sep. 6, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, and Ser. No. 115,152, Sep. 2, 1993.

[51] Int. Cl.$^6$ .................................................. A61M 5/20
[52] U.S. Cl. ........................ 606/185; 604/165; 604/170
[58] Field of Search ............................... 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy Tucker

[57] ABSTRACT

A safety penetrating instrument for penetrating an anatomical cavity wall to gain access to an anatomical cavity includes a penetrating member having a distal end for penetrating the anatomical cavity wall, a distally-biased safety member having a distal end movable between an extended position where the safety member distal end protrudes distally from the penetrating member distal end to protect the distal end of the penetrating member and a retracted position where the safety member distal end is disposed proximally of the penetrating member distal end to expose the penetrating member distal end, an extending mechanism for moving the safety member to the extended position and for permitting the safety member to move proximally toward the retracted position, a mechanism for manually moving the safety member proximally to the retracted position and a locking mechanism for locking the safety member in the retracted position to prevent movement of the safety member to the extended position during penetration of the anatomical cavity wall. The safety member can be a cannula movable proximally from the retracted position during penetration of the anatomical cavity wall and distally toward the retracted position in response to entry into the anatomical cavity, a safety shield or probe, or both a cannula and a safety shield or probe. A releasing mechanism for the safety penetrating instrument is responsive to movement of the cannula distally toward the retracted position to trigger release of the locking mechanism to permit the extending mechanism to move the safety member to the extended position.

33 Claims, 10 Drawing Sheets

U.S. PATENT DOCUMENTS

| | | |
|---|---|---|
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 3/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |
| 5,431,635 | 7/1995 | Yoon .................................. 604/165 |

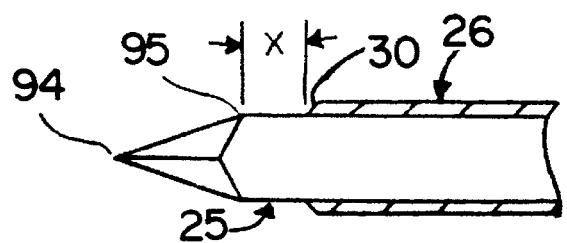
FIG. 9
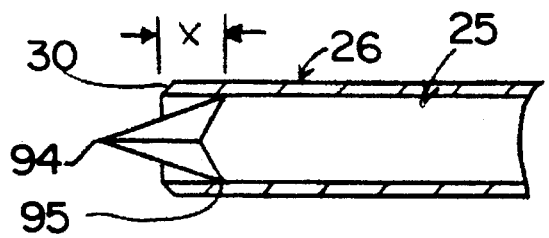
FIG. 10
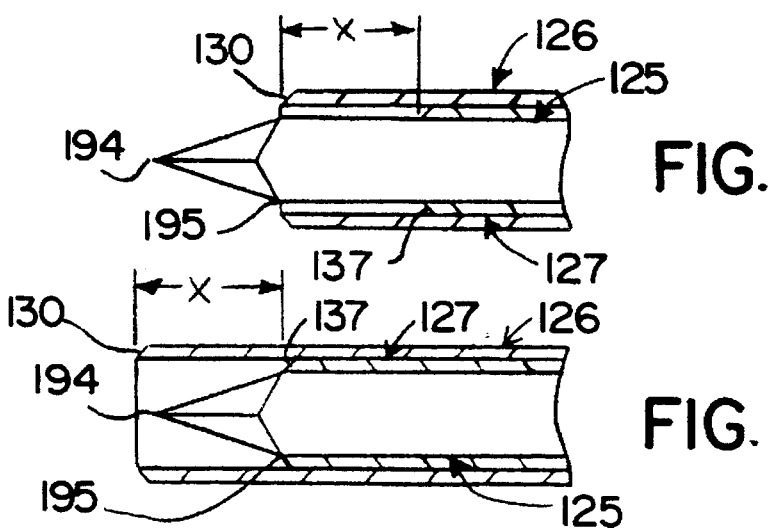
FIG. 11
FIG. 12
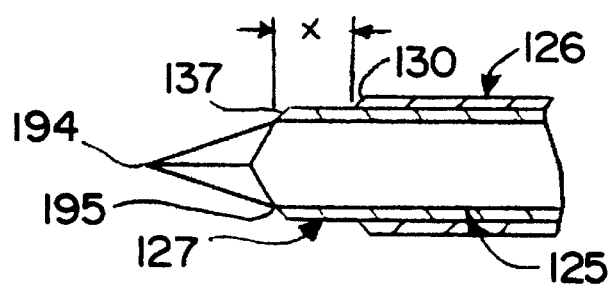
FIG. 13
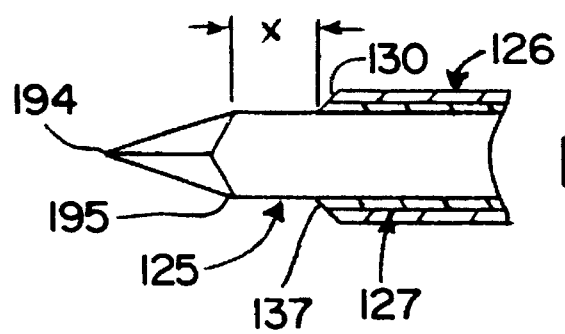
FIG. 14

SAFETY PENETRATING INSTRUMENT WITH CANNULA MOVING DURING PENETRATION AND TRIGGERED SAFETY MEMBER PROTRUSION

CROSS-REFERENCE TO RELATED APPLICATIONS

This application is a continuation-in-part of prior applications Ser. No. 08/083,220, filed Jun. 24, 1993, now U.S. Pat. No. 5,431,635, Ser. No. 08/083,728, filed Jun. 29, 1993, now U.S. Pat. No. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member with a distal end for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to use a cannula of a safety penetrating instrument as a safety member and to trigger distal movement of the cannula to an extended protruding position beyond a distal end of a penetrating member in response to distally-biased movement of the cannula upon penetration into an anatomical cavity.

Another object of the present invention is to use a safety shield or probe as a safety member in a safety penetrating instrument and to trigger distal movement of the safety shield or probe to an extended protruding position beyond a distal end of a penetrating member in response to distally-biased movement of the cannula upon penetration into an anatomical cavity.

Yet another object of the present invention is to use both a cannula and a safety shield or probe as safety members in a safety penetrating instrument and to trigger distal movement of the safety members to extended positions protruding beyond a distal end of a penetrating member in response to distally-biased movement of the cannula upon penetration into an anatomical cavity.

Some of the advantages of the safety penetrating instrument of the present invention are that the distal bias force on a safety member can be designed to assure protrusion of the safety member upon penetration regardless of the anatomical cavity being penetrated, that the force-to-penetrate of a safety penetrating instrument can be minimized to permit use in delicate tissue, that release of the safety member for movement to the extended protruding position can be triggered by slight distal movement of the cannula in response to penetration through the tissue, and that the safety penetrating instrument can be inexpensively manufactured with minimum components to reduce cost, facilitate sterilization for re-use and allow economical single-patient use.

The present invention is generally characterized in a safety penetrating instrument including a penetrating member having a distal end for penetrating an anatomical cavity wall to gain access to an anatomical cavity, a safety member having a distal end movable between an extended position where the safety member distal end is disposed distally of the penetrating member distal end to protect the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, means for manually moving the safety member proximally from the extended position to the retracted position and locking means for locking the safety member in the retracted position to prevent movement of the safety member to the extended position prior to penetrating into the anatomical cavity. The safety member can be a cannula, a safety shield or probe, or both a cannula and a safety shield or probe. Releasing means responsive to distally-biased movement of the cannula upon penetration into the anatomical cavity triggers release of the locking means to permit the extending means to move the safety member to the extended position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIGS. 9–14 are side views, partly in section, of alternative distal configurations for the safety penetrating instrument of the present invention prior to penetrating an anatomical cavity wall.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
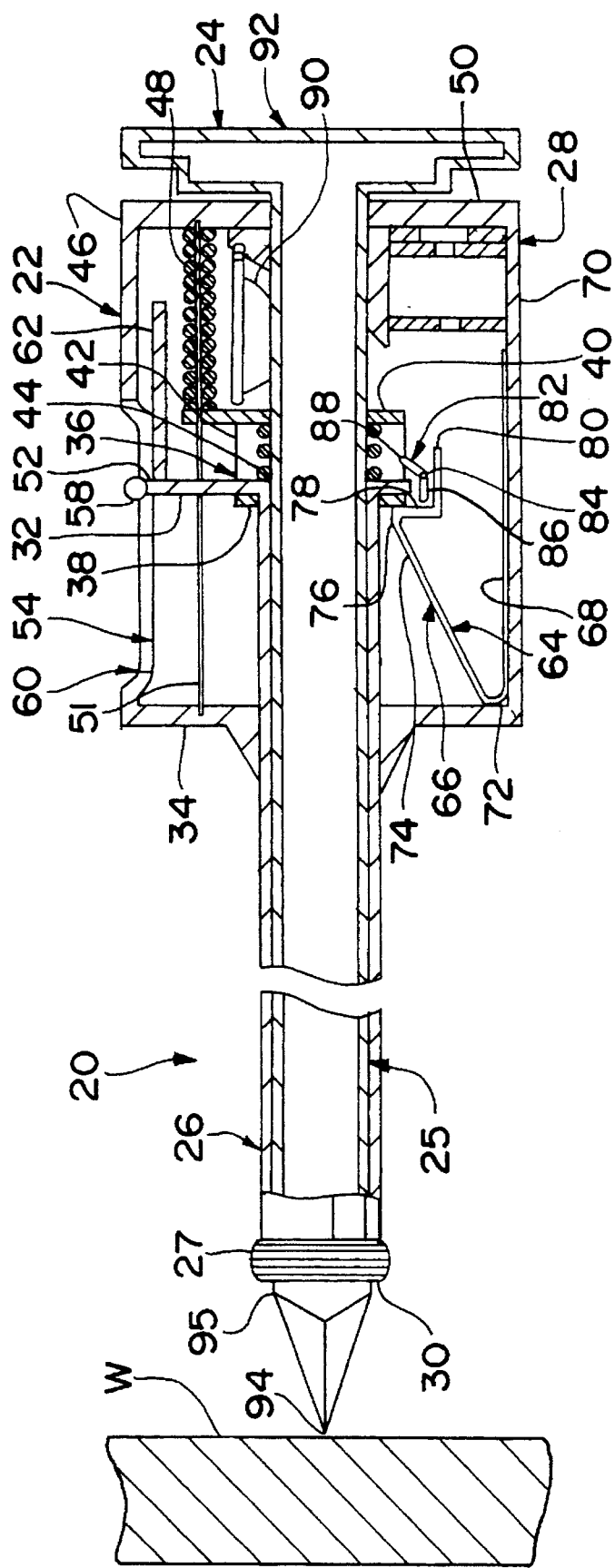
FIG. 1 is a broken side view, partly in section, of a safety penetrating instrument according to the present invention.

A safety penetrating instrument 20 according to the present invention, as shown in FIG. 1, is formed of a portal unit 22 and a penetrating unit 24. The portal unit 22 can be made of any desirable, medical grade materials depending on procedural use and desirability of being for single patient use or re-usable. The portal unit 22 includes an elongate portal sleeve, cannula or catheter 26 and a housing 28 mounting a proximal end of portal sleeve 26. Portal sleeve 26 terminates distally at a distal end 30 and proximally at a transverse flange 32 disposed in housing 28 with the portal sleeve passing through an opening in a front wall 34 of the housing. Portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 25 of penetrating unit 24.

A rail member 36 is disposed in housing 28 and is generally U-shaped including a forward wall 38 disposed transverse or perpendicular to a longitudinal axis of the penetrating instrument, a rearward wall 40 in configuration parallel to forward wall 38 and a side wall 42 transversely joining the forward and rearward rail member walls. Flange 32 is disposed between the rail member forward and rearward walls with the rail member forward wall 38 having an opening therein allowing passage therethrough by the portal sleeve 26. The rail member forward and rearward walls are disposed parallel or substantially parallel to flange 32, and a bias member 44 is connected between flange 32 and the rail member rearward wall 40 to bias the portal sleeve distally. As shown, bias member 44 includes a helical coil spring 44 disposed around the penetrating member 25 and mounted in compression between flange 32 and the rail member rearward wall 40 to bias the portal sleeve 26 distally to cause flange 32 to abut the rail member forward wall 38. However, bias member 44 can include various other types of springs as well as other types of bias devices including compression springs, tension springs, torsion springs, pan springs, leaf springs, rubber, plastic or magnets, for example. Rail member rearward wall 40 extends toward an upper wall 46 of housing 28, and an extending member 48 is mounted between rail member rearward wall 40 and a rear wall 50 of housing 28 to bias the portal sleeve 30 in a distal direction to an extended protruding position where distal end 28 of the portal sleeve is disposed beyond a sharp tip of the penetrating member 25 as will be explained further below. The extending member can include a helical coil spring 48 mounted in compression between rail member rearward wall 40 and the housing rear wall 50 as shown, or the extending member can include any other type of spring or other bias device as discussed for bias member 44. If desired, a guide rod 51 can be connected between the front wall 34 and the rear wall 50 of housing 28 with the spring 48 disposed around the guide rod.

Flange 32 extends toward the upper wall 46 of housing 28, and a pin 52 extends from flange 32 through a slot 54 in the housing upper wall 46 to terminate at a handle or knob 58 positioned in an elongate, trough-like recess 60 in the housing upper wall. Slot 54 and recess 60 extend longitudinally in parallel with the longitudinal axis of the safety penetrating instrument 20, and an indicator strip 62 extends proximally, perpendicularly from flange 30 to be visible through and along the length of slot 54 when the portal sleeve is in the extended protruding position as will be described further below. The indicator strip 62 can be colored and/or can be provided with any desirable indicia, and the slot 54 or the recess 60 can be provided with a transparent window or cover for viewing of the indicator strip therethrough.

A locking and releasing mechanism 64 for locking the portal sleeve in a retracted position, shown in FIG. 1, exposing the sharp distal end of the penetrating member and for releasing the portal sleeve to allow the portal sleeve to move to the extended protruding position includes a latch or locking spring 66, made of a strip of resilient material, formed to have a substantially flat base 68 secured to a bottom wall 70 of housing 28 and a bend 72 joining the base 68 with an upwardly angled arm 74 spaced from the base. Arm 74 carries or forms a latch 76 having a distal angled latching surface joining a proximal latching surface 78 disposed substantially transverse to the longitudinal axis of the safety penetrating instrument and substantially parallel to the rail member forward wall 38. Arm 74 has an extension 80 positioned proximally of latch 76, and a releasing member or trigger 82 is juxtaposed with extension 80. The trigger 82 is pivotally mounted in the housing on a pin 84 secured to a wall or walls of the housing or structure supported in the housing, and the trigger is generally L-shaped with a leg 86 overlying extension 80 and a leg 88 extending transversely from leg 86 but at a slight angle toward the proximal end of the safety penetrating instrument. A torsion spring (not shown) is coiled around pin 84 and fixed to trigger 82 to bias the trigger counterclockwise, looking at FIG. 1, such that leg 86 is biased toward extension 80.

The portal sleeve distal end 30 can have various configurations to protect tissue within an anatomical cavity by covering the distal tip of the penetrating member in the extended protruding position; and, as shown, the portal sleeve distal end defines an annular or peripheral edge having a blunt configuration to protect tissue within the anatomical cavity. The portal sleeve is provided with a shape or surface texture to increase resistance of the portal sleeve to passage through anatomical tissue such that the portal sleeve moves proximally against the bias of bias member 44 during penetration of anatomical tissue by the penetrating instrument. The resistance of the portal sleeve can be increased in many various ways such as by roughening, texturing or dimpling the external surface of the portal sleeve, providing the external surface with bumps, threads, ridges or other irregularities or by providing the portal sleeve with a formation, such as a slight enlargement or protrusion, having a configuration to increase the resistance of the portal sleeve 26 to penetration or passage through anatomical tissue to cause the portal sleeve to move proximally against the bias of spring 44 during penetration of anatomical tissue. Movement of the portal sleeve against the bias of bias member 44 can also be assured by selecting the strength of bias member 44 to cause proximal movement of the portal sleeve during penetration in response to a force from tissue contact such that the shape or external surface of the portal sleeve need not be modified and can be conventional. As shown in FIG. 1, the external surface of the portal sleeve 26 is ribbed or grooved and is slightly enlarged along a distal segment 27 adjacent the portal sleeve distal end to increase the resistance of the portal sleeve.

The housing 28 can be made of any desirable material and can have any desirable configuration to facilitate grasping by a user and includes a rear wall having an opening therein aligned with the opening in the housing front wall to allow passage therethrough by the penetrating member. The housing 28 is preferably constructed to sealingly engage instruments passing therethrough and to include a valve 90 biased to a closed state when no instrument passes through the portal sleeve. A flapper valve 90 is shown; however, any suitable valve construction can be utilized, for example, trumpet or nipple valves.

The penetrating unit 24 includes penetrating member 25 having an elongate shaft or body, a proximal end mounted to a hub 92, and a sharp distal end or tissue penetrating tip 94 extending from a transverse dimensional transition 95 in the shaft or body. The penetrating member distal end 94 can have any configuration desired by a user for a particular procedure, for example, the pyramidal trocar configuration shown or conical, threaded, multi-faceted or open, slanted or needle configurations. The penetrating member 25 can be made of any suitable, medical grade materials and can be made of multiple components such that, for example, the distal tip 94 is made of stainless steel and secured in any conventional manner, such as by threads, to the distal end of the shaft, which can be tubular and made of a less expensive material, such as plastic or metal. Hub 92 can be made of any desirable medical grade material and can have any desired configuration in cross-section to facilitate grasping of the hub and the housing by a user with one hand.

The portal unit 22 and the penetrating unit 24 can be provided to a user separately or assembled together as shown in FIG. 1, and either or both of the portal and penetrating units can be manufactured in a manner to be disposable for single patient use or to be sterilizable for re-use. The hub 92 can be coupled to the housing 28 by suitable detent or latch mechanisms if desired, and the penetrating unit can be withdrawn from the portal unit leaving the portal sleeve 26 in place within an anatomical cavity.

Figure 3:
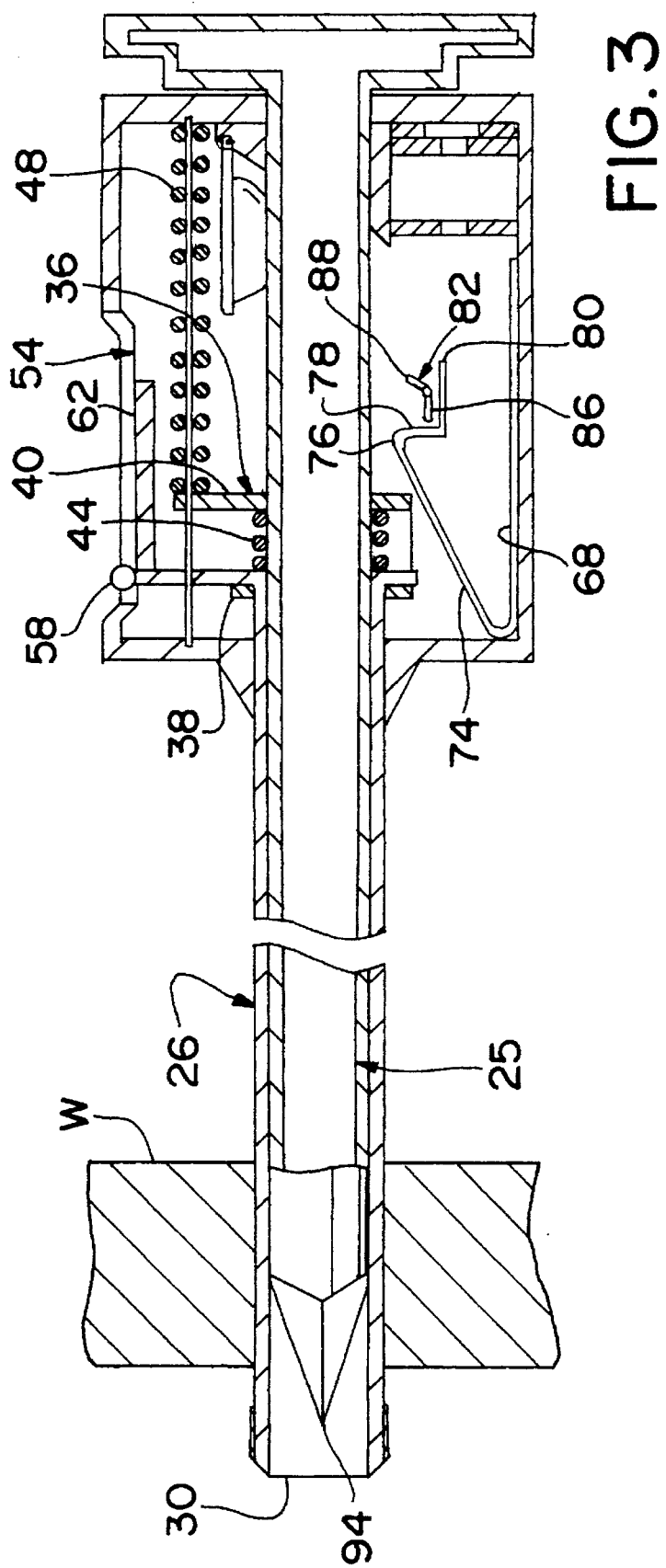
FIG. 3 is a broken side view, partly in section, of the safety penetrating instrument of FIG. 1 following penetration into the anatomical cavity.

In use, when a user desires to penetrate into an anatomical cavity using the safety penetrating instrument 20, the instrument is in the condition shown in FIG. 3 with the portal sleeve 26 in the extended protruding position to cover sharp distal tip 94 of the penetrating member 25. With the safety penetrating instrument 20 in the condition shown in FIG. 3, flange 32 will be in abutment with the forward wall 38 of rail member 36 due to the bias of bias member 44, and handle 58 will be disposed at a distal end of slot 54 due to the bias of extending member 48 with indicator strip 62 viewable along the length of the slot 54. Prior to commencing penetration of an anatomical wall W, handle 58 is grasped and manually moved proximally to move the portal sleeve 26 proximally against the bias of the extending member 48 until the forward wall 38 of rail member 36 rides over latch 76 by engaging the distal latching surface to move arm 74 toward base 68. At this time, the user can feel the rail member 36 lock into place in engagement with proximal latching surface 78 as arm 74 springs back and can also visually determine that the portal sleeve is locked in the retracted position by noting the position of handle 58 at a proximal end of slot 54 at which time the indicator strip 62 will no longer be visible or will be only slightly visible.

The safety penetrating instrument 20 is now in the position illustrated in FIG. 1 with the portal sleeve 26 locked in the retracted position by locking and releasing mechanism 64 and the penetrating member 25 extending from the distal end of the portal sleeve. With the portal sleeve 26 locked in the retracted position, portal sleeve distal end 30 will be disposed proximally of penetrating member tip 94, and flange 32 will be in abutment with the forward wall 38 of rail member 36 and will be disposed distally of leg 88 of trigger 82.

Figure 2:
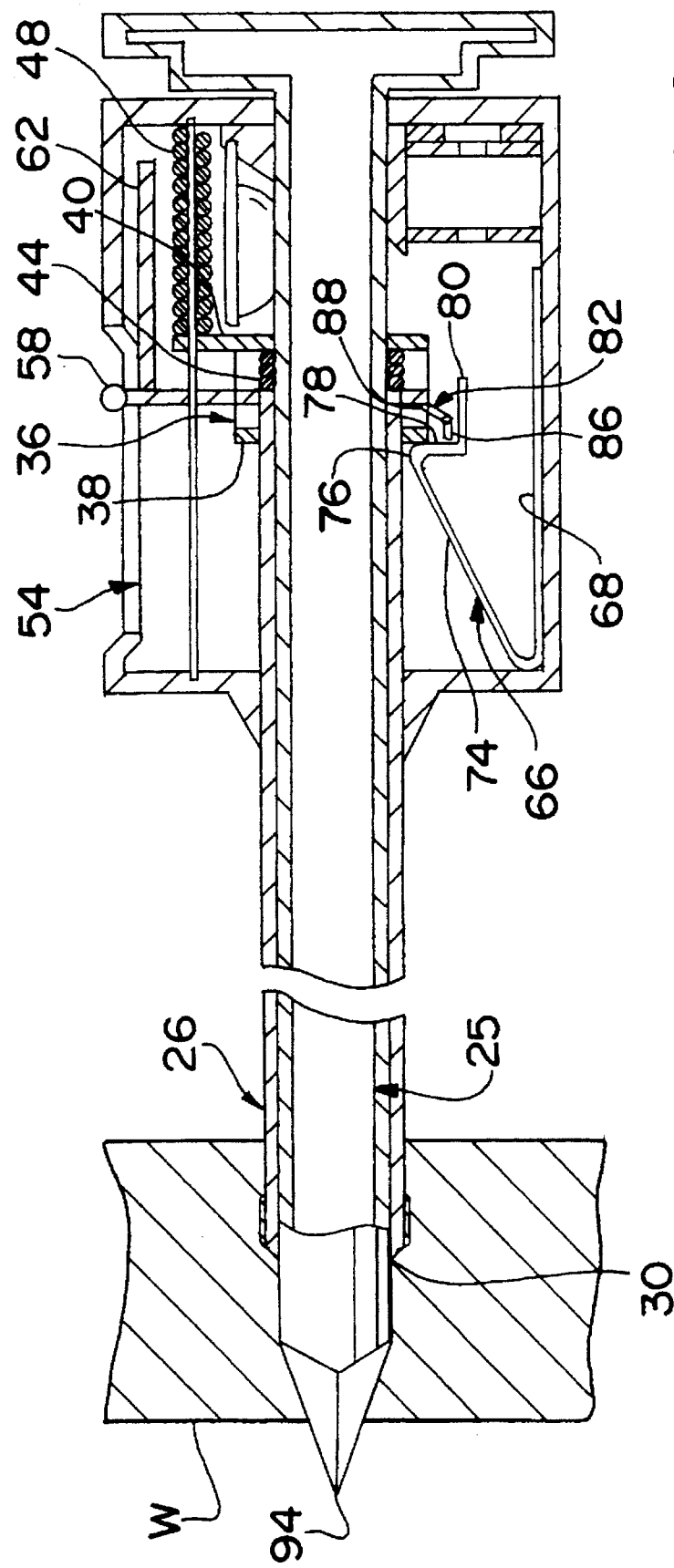
FIG. 2 is a broken side view, partly in section, of the safety penetrating instrument of FIG. 1 during penetration of a wall of an anatomical cavity.

As penetration of the anatomical cavity wall W is commenced, the force-to-penetrate is limited to the force required to cause sharp distal end 94 to pass through the cavity wall W since the penetrating member does not move during penetration. As penetration continues, the safety penetrating instrument will advance through the cavity wall W as shown in FIG. 2, and the force from tissue contact on the distal end of the portal sleeve 26 will cause the portal sleeve to move proximally causing the operating member formed by flange 32 to move proximally until flange 32 abuts the rearward wall 40 of rail member 36 which serves as a stop or abutment limiting proximal movement of the portal sleeve. As the flange 32 moves proximally, the operating member formed thereby engages leg 88 to pivot trigger 82 clockwise, looking at FIG. 2, to allow the operating member to pass thereby. The clockwise pivotal movement of trigger 82 does not cause movement of the latch 76 since there is no engagement by either leg 86 or 88 with arm extension 80. Once the operating member passes by leg 88, a torsion spring or the like returns trigger 82 to its normal position with leg 86 adjacent arm extension 80. Accordingly, during penetration of the anatomical cavity wall W, no force is required to overcome the bias of extending member 48.

Once the distal end 30 of the portal sleeve 26 has passed through the cavity wall W, a reduction in the force from tissue contact on the distal end of the portal sleeve will cause the portal sleeve to move distally due to the bias of bias member 44. As the portal sleeve 26 moves distally, flange 32 engages leg 88 of trigger 82 causing the trigger to pivot counterclockwise looking at FIG. 3 and causing leg 86 to engage arm extension 80 moving arm 74 toward base 68 against the force of spring strip 66. The movement of arm 74 away from the longitudinal axis of the safety penetrating instrument causes latch 76 to move out of engagement with the rail member forward wall 38 thereby allowing extending member 48 to move the portal sleeve further distally to the extended protruding position where distal end 30 protrudes beyond the sharp distal tip 94 of the penetrating member as illustrated in FIG. 3 thereby protecting tissue within the anatomical cavity from inadvertent contact with the sharp distal tip 94. With the distal end 30 of portal sleeve 26 in the anatomical cavity, the penetrating unit 24 can be withdrawn from the portal unit 22 leaving the portal sleeve in place such that instruments for performing endoscopic procedures can be introduced into the cavity via the portal formed by the portal unit 22.

Although the portal sleeve is disclosed herein as the safety member, it will be appreciated that the safety member can be any other member including a shield or probe. By forming extending member 48 to be relatively strong, protrusion of the safety member is assured even should the safety member engage tissue in the anatomical cavity wall or within the anatomical cavity or should any tissue be jammed between the safety member and the penetrating member and/or the portal sleeve. Additionally, the strong force of spring 48 provides the user with the psychological benefit of knowing the safety member is protecting the penetrating member. Should tissue within the anatomical cavity be contacted by the distal end of the safety member, the safety member can bounce or give a little in the manner of a shock absorber to protect such contacted tissue. Movement of the safety member can be seen by the user by noticing movement of the handle toward a distal end of the slot and observation of the indicator strip. The strong force of spring 48 also provides the user with an easily felt tactile signal that the safety member has moved to the extended position and that penetration into the cavity has occurred which also can be visually confirmed by the position of the handle and the indicator strip. The distal bias of spring 44 and/or the resistance of the portal sleeve need only be great enough to produce slight longitudinal movement of operating flange 32 past the trigger such that the force-to-penetrate is minimized. Release of the safety member to move distally to the extended protruding position can be triggered by distal movement of the safety member itself or of any other member. The safety member can have various configurations so long as the distal end protrudes beyond the sharp tip of the penetrating member to provide a protective function, and a plurality of safety members can be employed in the safety penetrating instrument.

Figure 4:
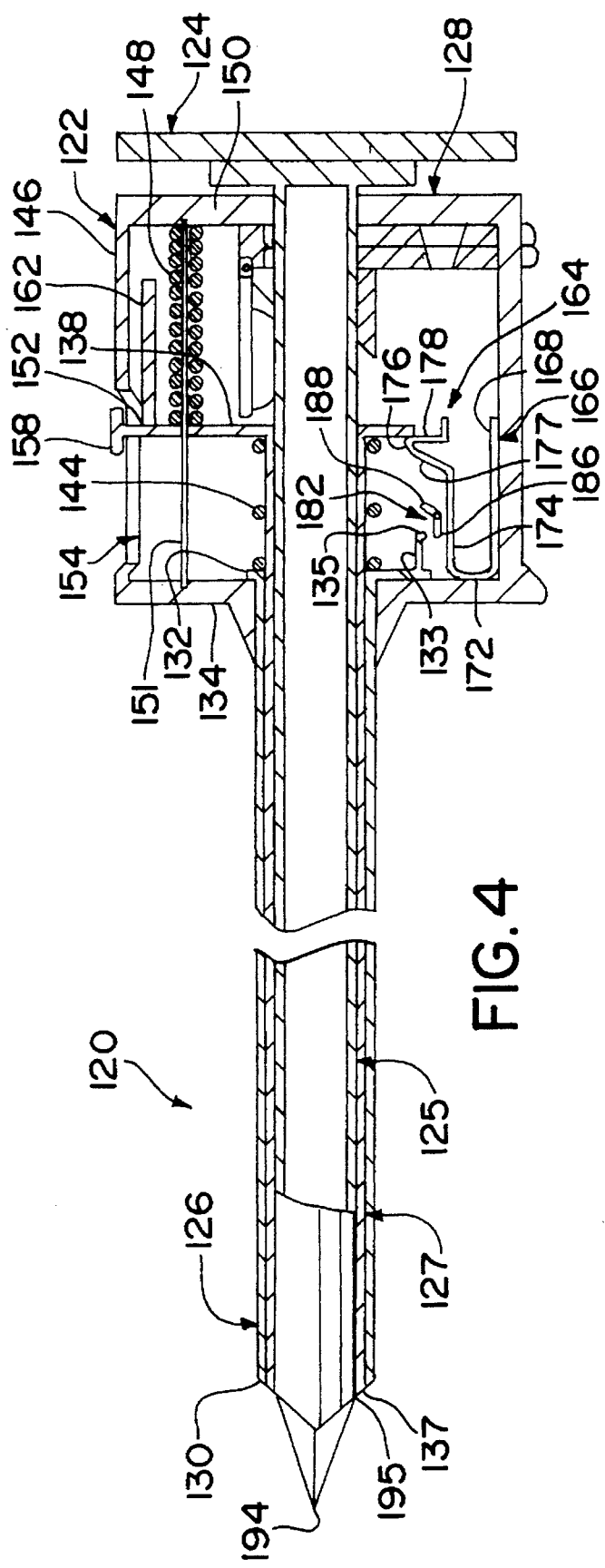
FIG. 4 is a broken side view, partly in section, of a modification of a safety penetrating instrument according to the present invention.

A modification of the safety penetrating instrument according to the present invention is shown at 120 in FIG. 4. Safety penetrating instrument 120 is similar to safety penetrating instrument 20 except that the safety member for safety penetrating instrument 120 includes a safety shield, and movement of the safety shield to the extended protruding position is triggered by movement of the portal sleeve in response to a reduction in the force from tissue contact following entry in the anatomical cavity. Safety penetrating instrument 120 includes a portal unit 122 and a penetrating unit 124, the penetrating unit 124 being similar to penetrating unit 24. Portal unit 122 is similar to portal unit 22 and includes portal sleeve 126, safety shield 127 and housing 128. Portal sleeve 126 is similar to portal sleeve 26 except that portal sleeve 126 is provided without textured segment 27. Portal sleeve 126 terminates distally at distal end 130 and proximally at flange 132 disposed in housing 128. Flange 132 is similar to flange 32 except that flange 132 has a finger 133 extending perpendicularly or transversely therefrom in a proximal direction to terminate at a barb 135.

Safety shield 127 is disposed in portal sleeve 126 and terminates distally at a distal end 137 and proximally at a transverse flange or plate 138 disposed in housing 128. Safety shield 127 can have any desirable configuration in cross-section to couple safety shield distal end 137 with plate 138. A bias member 144 including a helical coil spring is disposed around the safety shield 127 and held in compression between flange 132 and plate 138 to bias the portal sleeve 126 in a distal direction to cause flange 132 to abut front wall 134 of housing 128. The strength of spring 144 is selected to allow proximal movement of portal sleeve 126 in response to the force from tissue contact during penetration of an anatomical cavity wall and to cause distal movement of the portal sleeve in response to a reduction in the force from tissue contact upon penetration into the anatomical cavity. An extending member 148 including a helical coil spring is connected between plate 138 and a rear wall 150 of housing 128 to bias the safety shield to an extended protruding position where the distal end 137 of the safety shield is disposed beyond the distal end 194 of the penetrating member 125; and, if desired, spring 148 can be disposed around a guide rod 151 connected between the forward wall 134 and the rearward wall 150 of the housing. Plate 138 extends toward upper wall 146 of housing 128, and a pin 152 extends from plate 138 through slot 154 in the housing upper wall 146 to terminate at a handle or knob 158. An indicator strip 162 extends proximally, perpendicularly from plate 138 to be visible through and along the length of slot 154 when the safety shield is in the extended protruding position as will be described further below.

Safety penetrating instrument 120 includes a locking and releasing mechanism 164 for locking the safety shield 127 in a retracted position exposing the sharp distal tip 194 of the penetrating member 125 and releasing the safety shield to allow the safety shield to move to the extended protruding position. Locking and releasing mechanism 164 is similar to locking and releasing mechanism 64 except that trigger 182 for locking and releasing mechanism 164 is disposed distally of a protruding latch 176. The latch or locking spring 166 for locking and releasing mechanism 164 is made of a strip of resilient material formed to have a substantially flat base 168 secured to a bottom wall of housing 128 and a bend 172 joining the base 168 with an arm 174 disposed parallel or substantially parallel with a longitudinal axis of the safety penetrating instrument 120 and with base 168. Arm 174 carries latch 176 which has a distal angled latching surface 177 joining a proximal latching surface 178 disposed substantially transverse to the longitudinal axis of the safety penetrating instrument and substantially parallel to the plate 138. Trigger 182 is juxtaposed with arm 174 to be disposed distally of latch 176 and is similar to trigger 82 with a leg 186 overlying arm 174 and a leg 188 extending substantially transversely from leg 186 but at a slight angle toward the proximal end of the safety penetrating instrument. Trigger 182 is biased counterclockwise, looking at FIG. 4, such that leg 186 is biased toward arm 174.

Use of the safety penetrating instrument 120 is similar to that described above with respect to safety penetrating instrument 20 in that, when a user desires to penetrate into an anatomical cavity, the safety penetrating instrument will normally be provided with the safety shield 127 in the extended protruding position where the distal end 137 of the safety shield protrudes beyond the penetrating member distal end 194. The safety shield 127 will be biased to the extended protruding position by extending member 148 such that handle 158 will be disposed at a distal end of slot 154 with plate 138 disposed distally of latch 176. The portal sleeve 126 will be biased distally by bias member 144 with flange 132 biased in abutment with housing forward wall 134.

Prior to commencing penetration of an anatomical cavity wall, handle 158 is grasped and manually moved proximally to move safety shield 127 proximally against the bias of extending member 148 until plate 138 rides over latch 176 by engaging distal latching surface 177 to move arm 174 toward base 168. The safety shield 127 will then be locked in the retracted position due to engagement of plate 138 with proximal latching surface 178 as shown in FIG. 4. As previously noted, the user can feel the plate lock into place in engagement with latch 176 and can also visually determine that the safety shield is in the locked retracted position by noting the position of the handle 158 at a proximal end of slot 154 at which time indicator strip 162 will no longer be visible or will be only slightly visible along the slot. With the safety shield 127 locked in the retracted position, the distal end 137 of the safety shield and the distal end 130 of the portal sleeve will be disposed proximally of the sharp tip 194 of the penetrating member, and flange 132 will remain biased by spring 144 into abutment with housing forward wall 134 with barb 135 disposed distally of trigger 182.

With the safety penetrating instrument 120 in the position illustrated in FIG. 4, penetration of the cavity wall is commenced, and the force from tissue contact on the distal end 130 of the portal sleeve 126 will cause the portal sleeve to move proximally against the bias of spring 144 causing barb 135 to move past trigger leg 188 without causing movement of latch 176; and, accordingly, the barb 135 is now positioned proximally of the trigger 182. Upon entry into the anatomical cavity, the counterforce on the distal end of the portal sleeve will be reduced allowing spring 144 to move the portal sleeve distally causing barb 135 to engage leg 188 of trigger 182 and pivot the trigger counterclockwise causing leg 186 to engage arm 174. The engagement of leg 186 with arm 174 causes arm 174 to move toward base 168 moving the latch 176 out of engagement with plate 138 thereby allowing spring 148 to cause the safety shield to move distally to the extended protruding position wherein the safety shield distal end 137 protrudes beyond the distal end 194 of penetrating member 125. The penetrating unit 124 can then be withdrawn from the portal unit 122 leaving the portal sleeve 126 and the safety shield 127 in place.

Figure 5:
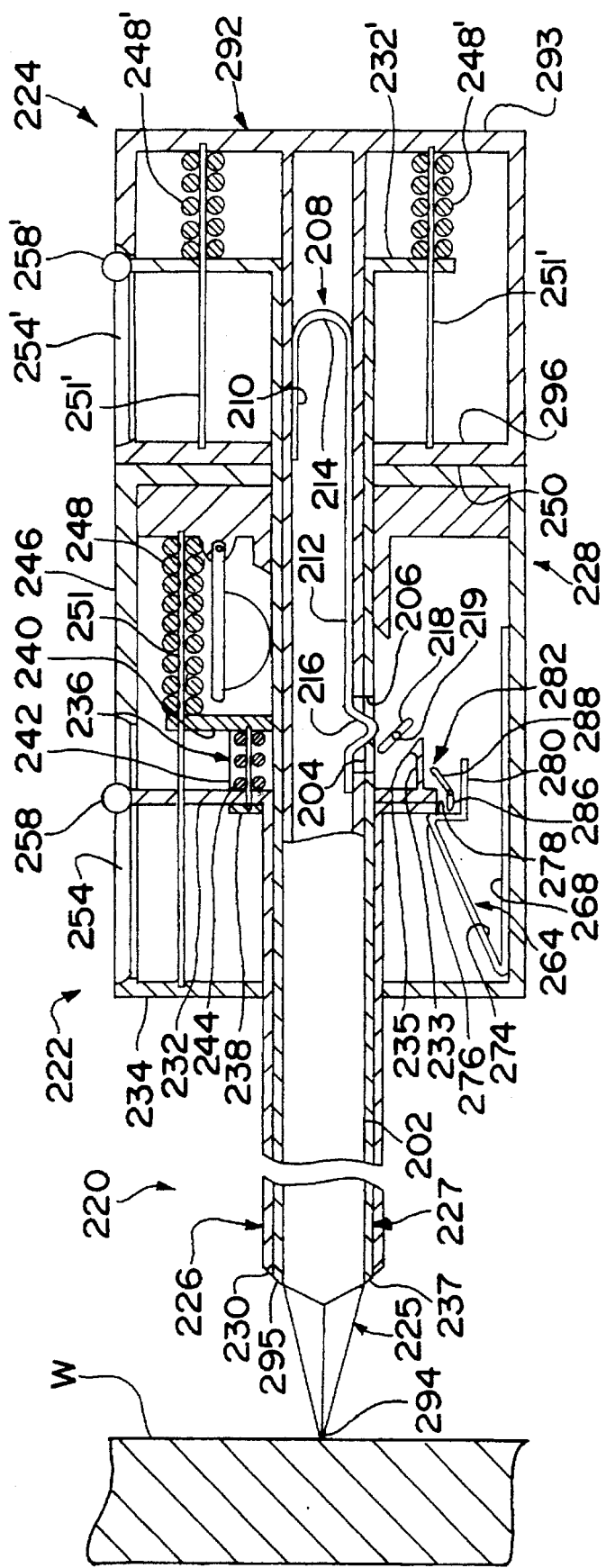
FIG. 5 is a broken side view, partly in section, of a further modification of a safety penetrating instrument according to the present invention.

Another modification of a safety penetrating instrument according to the present invention is shown in FIG. 5 at 220. Safety penetrating instrument 220 is similar to safety penetrating instrument 120 except that the safety shield for the safety penetrating instrument 220 is part of the penetrating unit and both the portal sleeve and safety shield are triggered to move to extended protruding positions to serve as safety members upon penetration of the portal sleeve into the anatomical cavity. Safety penetrating instrument 220 includes a portal unit 222 and penetrating unit 224. Portal unit 222 is similar to portal unit 22 and includes a portal sleeve 226 and a housing 228 mounting the proximal end of the portal sleeve. Portal sleeve 226 is similar to portal sleeve 26 except that portal sleeve 226 is provided without textured segment 27. Portal sleeve 226 terminates distally at distal end 230 and proximally at flange 232 disposed in housing 228. Flange 232 is similar to flange 32 except that flange 232 has a finger 233 extending transversely or perpendicular therefrom in a proximal direction relative to flange 232 to terminate at a barb 235. A rail member 236 is disposed in housing 228 and is generally U-shaped including a forward wall 238 disposed transverse or perpendicular to a longitudinal axis of the penetrating instrument, a rearward wall 240 in configuration parallel to forward wall 238 and a side wall 242 transversely joining the forward and rearward rail member walls. Flange 232 is disposed between the rail member forward and rearward walls with the rail member forward wall 238 having an opening therein allowing passage therethrough by the portal sleeve 226. The rail member forward and rearward walls are disposed parallel or substantially parallel to flange 232, and a bias member 244 is connected between flange 232 and the rail member rearward wall 240 to bias the portal sleeve distally. As shown, bias member 244 includes a helical coil spring 244 in compression between flange 232 and the rail member rearward wall 40 to bias the portal sleeve 226 distally to cause flange 232 to abut the rail member forward wall 238. However, bias member 244 can include various other types of springs as well as other types of bias devices including compression springs, tension springs, torsion springs, pan springs, leaf springs, rubber, plastic or magnets, for example. Rail member rearward wall 240 extends toward an upper wall 246 of housing 228, and an extending member 248 is mounted between rail member rearward wall 240 and a rear wall 250 of housing 228 to bias the portal sleeve 226 in a distal direction to an extended protruding position where distal end 228 of the portal sleeve is disposed beyond the sharp tip 294 of penetrating member 225. The extending member can include a helical coil spring 248 mounted in compression between rail member rearward wall 240 and the housing rear wall 250 as shown, or the extending member can include any other type of spring or other bias device as discussed for bias member 244. If desired, a guide rod 251 can be connected between the front wall 234 and the rear wall 250 of housing 228 with the spring 248 disposed around the guide rod.

Penetrating unit 224 includes penetrating member 225, safety shield 227 and hub 292 mounting proximal ends of the penetrating member and the safety shield. Safety shield 227 is disposed in portal sleeve 226 and terminates distally at a distal end 237 and proximally at a transverse flange or plate 232' disposed in hub 292. Safety shield 227 can have any desirable configuration in cross-section to couple safety shield distal end 237 with flange 232'. Extending members 248' including helical coil springs are connected between flange 232' and a rear wall 293 of hub 292 to bias the safety shield to an extended protruding position where the distal end 237 of the safety shield is disposed beyond the distal end 294 of the penetrating member 225; and, if desired, springs 248' can be disposed around respective guide rods 251' connected between the forward and rearward walls 296 and 293 of the hub.

Penetrating member 225 is similar to penetrating member 125 and has a sharp distal end or tip 294 and a proximal end secured to the rear wall 293 of hub 292. As shown, penetrating member 225 includes a hollow cylindrical or tubular main body 202 having an opening or slot 204 formed intermediate proximal and distal ends of the penetrating member in alignment with a similar opening 206 formed in safety shield 227. A latching spring clip 208 is mounted within the penetrating member main body 202 and includes a generally U-shaped member formed from a strip of resilient material to have a pair of longitudinal legs 210 and 212 contacting diametrically opposed portions of the internal surface of penetrating member main body 202 and being joined at respective proximal ends by a curved transverse section 214. Legs 210 and 212 are of unequal length and are normally biased apart. The longer leg 212 has a distal portion 216 configured to protrude through slots 204 and 206 in the penetrating member and safety shield to lock the safety shield 227 in the retracted position and to prevent distal movement of the shield relative to the penetrating member.

Locking and releasing mechanism 264 for safety penetrating instrument 220 is similar to locking and releasing mechanism 64 for safety penetrating instrument 20 and includes a latch 276 for locking the portal sleeve rail member 236 in the retracted position and a trigger 282 for releasing the rail member to move the portal sleeve to the extended protruding position. Additionally, a lever 218 is rotatably mounted on a pin 219 extending perpendicularly between walls of the housing 228 adjacent the protruding spring clip distal portion 216 of the safety shield 227 and the barb 235 carried at the proximal end of portal sleeve finger 233. A torsion spring (not shown) is attached between the lever 218 and the pin 219 to bias the lever in a clockwise direction looking at FIG. 5 and into contact with the protruding spring clip distal portion 216.

Handles 258 and 258' are coupled with the portal sleeve 226 and safety shield 227, respectively, for movement along slots 254 and 254' formed in the housing 228 and hub 292, respectively, to move the portal sleeve and safety shield from their extended protruding positions to locked retracted positions as previously explained above.

Figure 8:
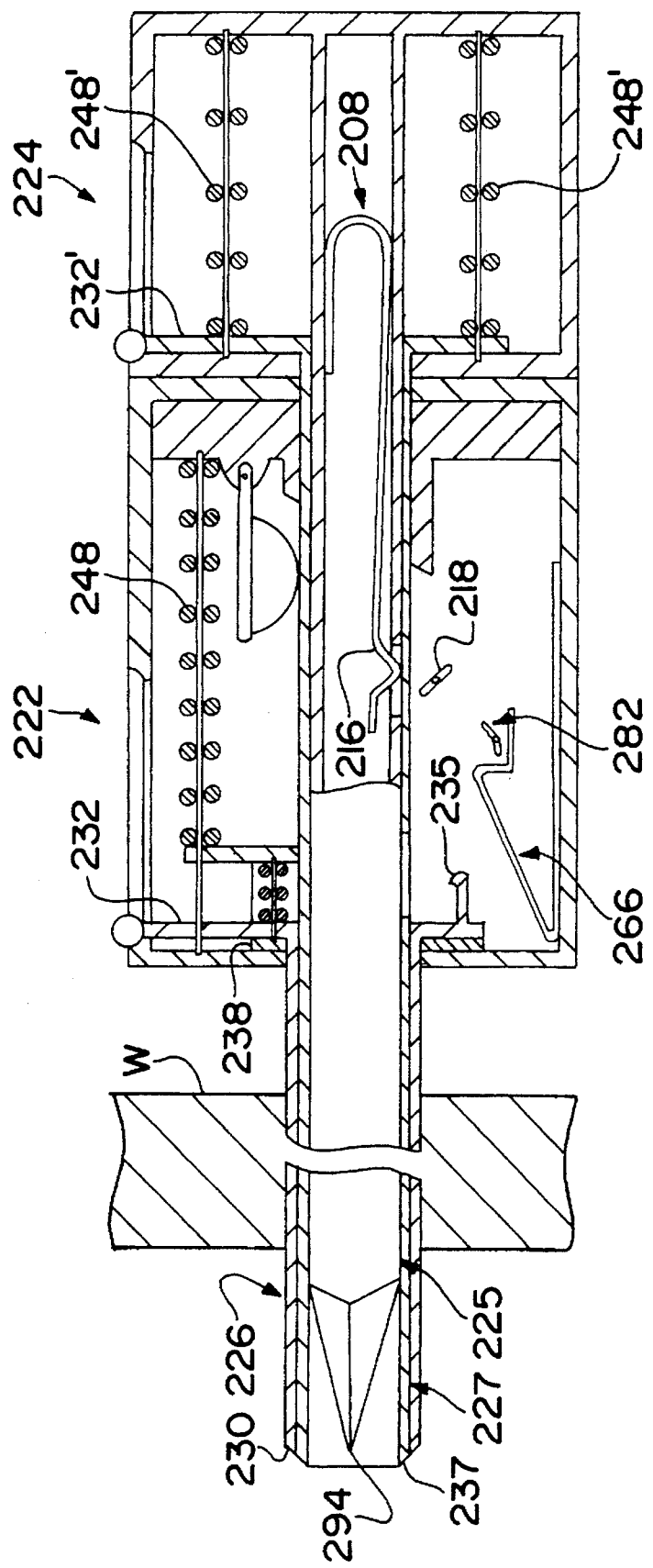
FIG. 8 is a broken side view, partly in section, of the safety penetrating instrument of FIG. 5 following penetration into the anatomical cavity.

Use of the safety penetrating instrument 220 is similar to that previously described; however, both the portal sleeve 226 and the safety shield 227 will initially be in the extended protruding position shown in FIG. 8 with the portal sleeve distal end 230 and the safety shield distal end 237 disposed beyond the distal end 294 of penetrating member 225 to protect the sharp tip of the penetrating member. In order to move the portal sleeve and safety shield to the retracted positions shown in FIG. 5, handles 258 and 258' are grasped one at a time or simultaneously to move the portal sleeve and safety shield proximally until the portal sleeve rail member forward wall 238 rides over latch 276 to be latched in the retracted position with the rail member forward wall 238 locked against proximal latching surface 278 and slots 204 and 206 in the penetrating member and safety shield are aligned allowing the distal portion 216 of spring clip 208 to pop through the aligned slots to lock the shield in the retracted position. As previously noted, the user can feel the rail member forward wall 238 lock into place in engagement with the latch 276 and can also visually determine that the safety shield and portal sleeve are locked in retracted positions by noting the position of the handles 258 and 258' at proximal ends of their respective slots.

Figure 6:
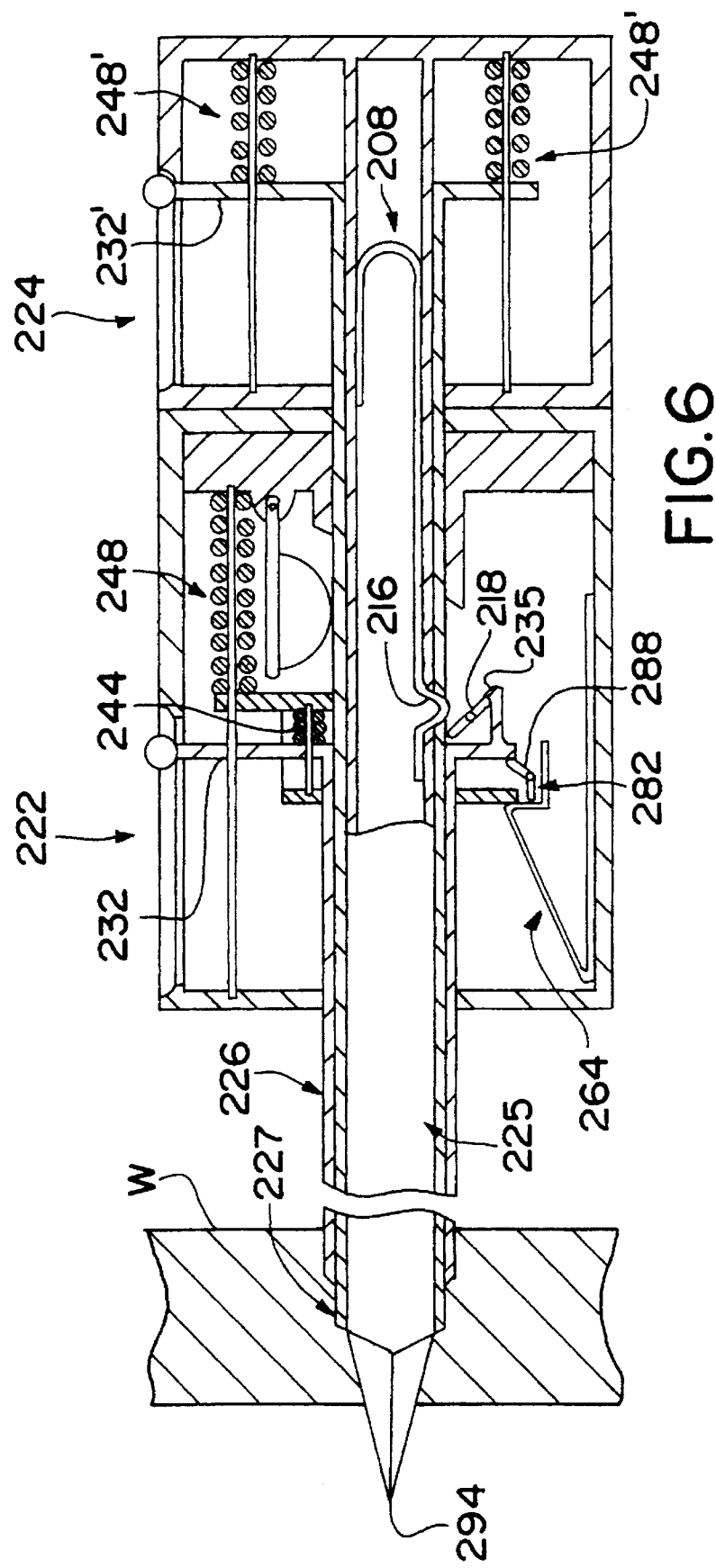
FIG. 6 is a broken side view, partly in section, of the safety penetrating instrument of FIG. 5 during penetration of an anatomical cavity wall.

With the safety penetrating instrument 220 in the locked retracted position illustrated in FIG. 5, the respective distal ends of the portal sleeve and safety shield will be disposed proximally of the distal tip of the penetrating member. The safety shield is locked against movement relative to the penetrating member so only the portal sleeve is able to move between forward and rear rail member walls. Penetration of a cavity wall W is commenced, and the force from tissue contact on the distal end 230 of the portal sleeve 226 will cause the portal sleeve to move proximally against the bias of bias member 244 causing flange 232 to move past trigger leg 288 and barb 235 to move past lever 218. Movement of flange 232 proximally past trigger leg 288 does not cause movement of latch 276 since there is no contact of trigger leg 286 with arm extension 280; and, accordingly, flange 232 is then positioned proximally of trigger leg 288 as shown in FIG. 6. Similarly, movement of barb 235 proximally past lever 218 does not cause movement of spring clip 208 since the lever 218 is made to rotate counterclockwise looking at FIG. 6 away from the protruding distal portion 216 of the spring clip.

Figure 7:
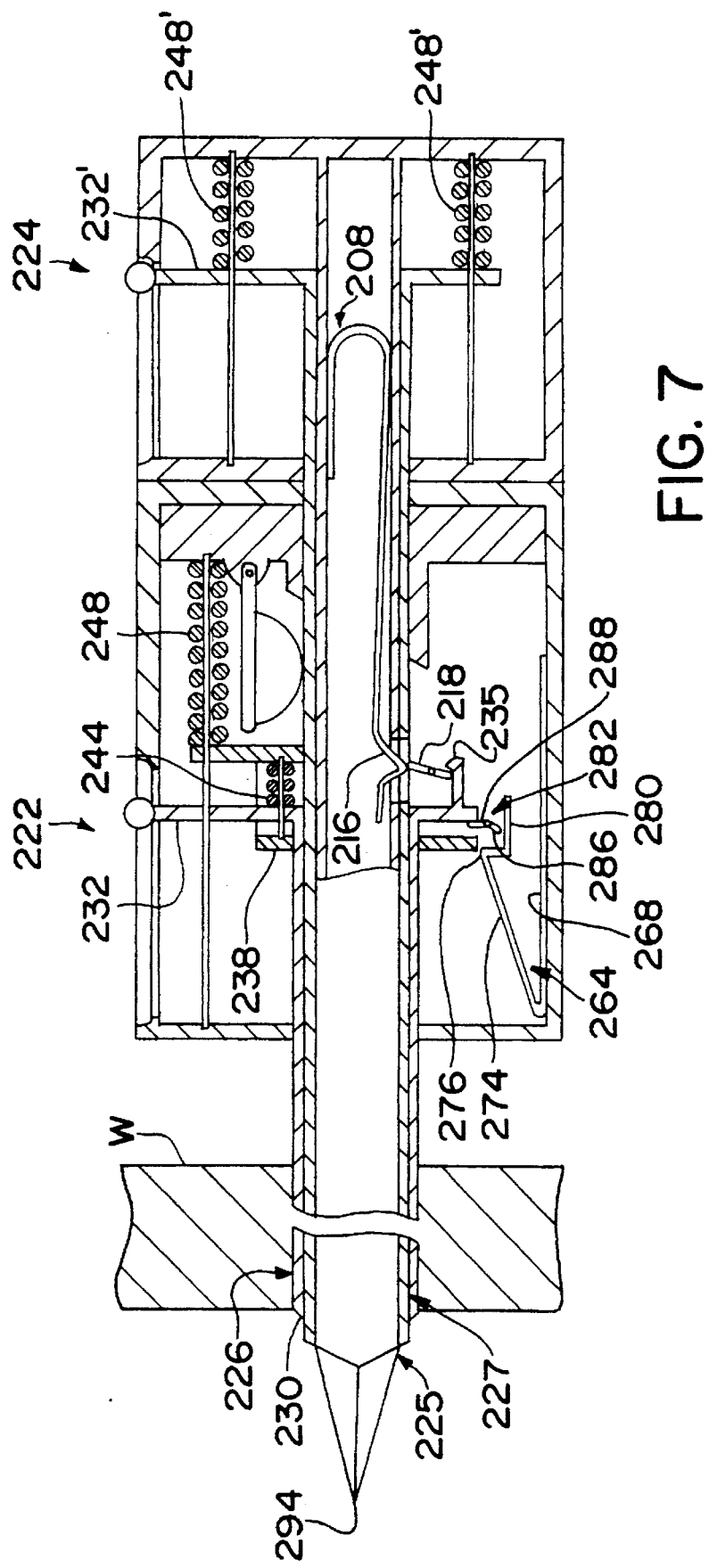
FIG. 7 is a broken side view, partly in section, of the safety penetrating instrument of FIG. 5 immediately prior to penetrating through the anatomical cavity wall.

Upon entry into the anatomical cavity, the counter force on the distal end 230 of the portal sleeve will be reduced allowing bias member 244 to move the portal sleeve distally causing flange 232 to engage trigger leg 288 and pivot the trigger 282 counterclockwise looking at FIG. 7 causing leg 286 to engage arm extension 280. The engagement of leg 286 with arm extension 280 causes arm 274 to move toward base 268 moving the latch 276 out of engagement with the rail member forward wall 238 thereby allowing spring 248 to cause the portal sleeve to move further distally to the extended protruding position wherein portal sleeve distal end 230 protrudes beyond the distal end 294 of the penetrating member as shown in FIG. 8. Simultaneously, barb 235 is carried along proximally with portal sleeve flange 232 and engages the lever 218 causing the lever 218 to rotate clockwise looking at FIG. 7 and to cam the protruding distal portion 216 of spring clip 208 into the hollow cavity defined within the penetrating member. Displacement of the protruding distal portion 216 of spring clip 208 into the penetrating member releases the safety shield 227 allowing the safety shield 227 to move distally under the influence of springs 248' to protrude beyond the distal end 294 of the penetrating member 225 as shown in FIG. 8. The penetrating unit 224 including the penetrating member 225 and the safety shield 227 can then be withdrawn from the portal unit 222 leaving the portal sleeve 226 in place.

From the above, it will be appreciated that the portal sleeve or cannula of the safety penetrating instrument of the present invention is movable proximally during penetration of an anatomical cavity wall and distally upon entering the anatomical cavity to trigger further distal movement or protrusion of the cannula, protrusion of a safety shield or probe, or protrusion of both the cannula and a safety shield or probe to function as safety members protecting the distal end of the penetrating member. By "safety member" is meant any structure movable distally relative to the penetrating member to protect the tip of the penetrating member within an anatomical cavity. Since in the safety penetrating instrument of the present invention one or both of a cannula and a safety shield or probe can be extended to protect the penetrating member tip, each can function as a safety member upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and a penetrating member, a safety probe fitted within a hollow penetrating member, or a component partly within and around the penetrating member and movable distally to protrude relative to the penetrating member to protect the distal end thereof when triggered. On the other hand, if the cannula does function as a safety member, it can be coupled with a protective sheath or probe that is not triggered to protrude or with any of the aforementioned safety members. Redundant safety can also be achieved by biasing the safety shield and/or penetrating member distally while allowing one or both to move proximally during penetration and triggering release of the safety member in response to distal movement of one or more of the cannula, the safety shield and the penetrating member upon entry into the anatomical cavity. Additionally, the triggered safety member protrusion can be combined with penetrating member retraction to provide separate modes of safety.

In the embodiments shown, the distal end of the cannula, and the distal end of the safety shield or probe if provided, are aligned with a transverse dimensional transition in the penetrating member at the penetrating member distal end immediately prior to use in penetrating the anatomical cavity wall; and since the cannula is movable during penetration, the distal end of the cannula becomes displaced proximally relative to the penetrating member during penetration, triggering safety member protrusion when moving distally toward the aligned position upon entering the anatomical cavity.

FIG. 9 shows an alternative distal configuration for safety penetrating instrument 20 wherein the distal end 30 of the portal sleeve or cannula 26 is located proximally of the penetrating member distal end transition 95 prior to use. In this configuration the portal sleeve distal end 30 will begin to move further proximally after the penetrating member 25 has penetrated the anatomical cavity wall to a predetermined depth X and will spring back to its original position proximal of the penetrating member distal end transition 95 upon entering into the anatomical cavity thereby triggering protrusion of the portal sleeve beyond the penetrating member distal end 94 to function as a safety member.

Another distal configuration for safety penetrating instrument 20 is shown in FIG. 10 wherein the distal end 30 of the cannula or portal sleeve 26 is spaced distally of the penetrating member distal end transition 95 a predetermined distance X preferably corresponding to the distance between rail member forward and rear walls. In this configuration the portal sleeve distal end 30 will move proximally during penetration towards becoming aligned with the distal end transition 95 of the penetrating member 25 to ease penetration by providing a smooth profile and will spring back beyond the penetrating member distal end 94 upon entering into the anatomical cavity thereby triggering further distal movement or protrusion beyond the penetrating member distal end 94 by the cannula 26.

FIG. 11 shows an alternative distal configuration for the safety penetrating instruments 120 and 220 (hereinafter described with reference to safety penetrating instrument 120) wherein the distal end 130 of the portal sleeve or cannula 126 is aligned with the penetrating member distal end transition 195 prior to use and the safety shield distal end 137 is spaced proximally of the portal sleeve distal end 130 a predetermined distance X preferably corresponding to the distance between rail member forward and rear walls. In this configuration the portal sleeve distal end 130 will move proximally during penetration towards becoming aligned with the safety shield distal end 137 and will spring back into alignment with the penetrating member distal end transition 195 upon entering into the anatomical cavity thereby triggering protrusion beyond the penetrating member distal end 194 by the portal sleeve, safety shield or both the portal sleeve and safety shield.

FIG. 12 shows another alternative distal configuration for the safety penetrating instruments 120 and 220 (hereinafter described with reference to safety penetrating instrument 120) wherein the distal end 137 of the safety shield 127 is aligned with the penetrating member distal end transition 195 prior to use and the distal end 130 of the portal sleeve or cannula 126 is spaced distally of the safety shield distal end 137 a predetermined distance X preferably corresponding to the distance between rail member forward and rear walls. In this configuration the portal sleeve distal end 130 will move proximally during penetration towards becoming aligned with the distal end transition 195 of the penetrating member 125 and the safety shield distal end 137 to ease penetration and will spring back beyond the penetrating member distal end 194 upon entering into the anatomical cavity thereby triggering protrusion beyond the penetrating member distal end 194 by the safety shield.

Another alternative distal configuration for safety penetrating instruments 120 and 220 (hereinafter described with reference to safety penetrating instrument 120) is shown in FIG. 13 wherein the distal end 137 of the safety shield 127 is aligned with the penetrating member distal end transition 195 prior to use and the distal end 130 of the portal sleeve or cannula 126 is spaced proximally of the safety shield distal end 137 a predetermined distance X to delay proximal movement of the portal sleeve 126. In this configuration the portal sleeve distal end 130 will move proximally during penetration after the penetrating member 125 and safety shield 127 have penetrated the anatomical cavity wall to a depth approximately equal to the distance X. The portal sleeve 126 will spring back distally upon entering the anatomical cavity thereby triggering further distal movement or protrusion of the portal sleeve, the safety shield or both the portal sleeve and safety shield to serve as safety members.

Yet another distal configuration for safety penetrating instruments 120 and 220 (hereinafter described with reference to safety penetrating member 120) is shown in FIG. 14 wherein distal ends 130 and 137 of both the portal sleeve 126 and the safety shield 127 are located proximally of the penetrating member distal end transition 195 a predetermined distance X. In this configuration, the portal sleeve 126 will begin to move proximally relative to the safety shield 127 and penetrating member 125 when the penetrating member 125 has penetrated into the anatomical cavity wall a distance approximately equal to X and will trigger protrusion of the portal sleeve, the safety shield or both upon moving back distally toward the distal end of the safety shield.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield or probe can be chamfered or blunt, smooth or roughened, or have any other configuration depending on the need for ease of penetration or increased resistance; and when a safety shield or probe is provided it can be mounted either by the portal unit or the penetrating unit depending on the desirability of being left in place with the cannula or withdrawn with the penetrating member.

Figure 15:
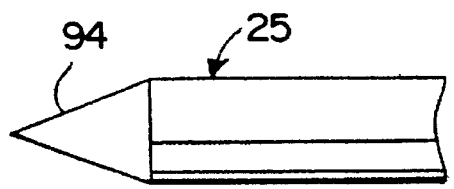
FIGS. 15–20 are side views of alternative distal configurations for the penetrating member of the safety penetrating instrument of the present invention.
Figure 16:
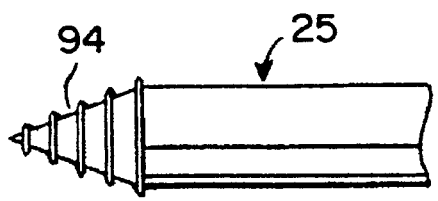
Figure 17:
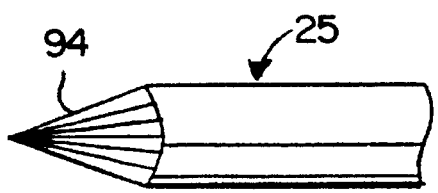
Figure 18:
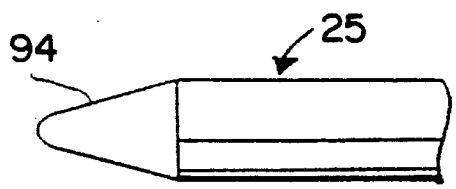
Figure 19:
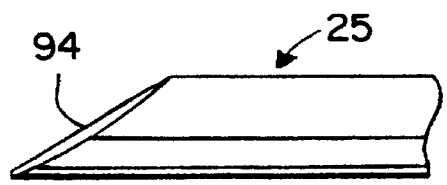
Figure 20:
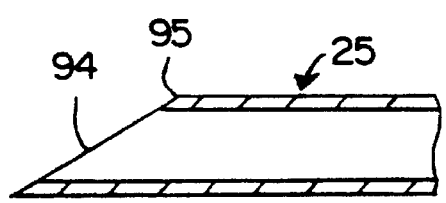

The penetrating member can be solid, hollow or partially solid and hollow, formed as single or multiple pieces, and fixedly mounted as shown or movable telescopically over a guide tube or the like. The distal end 94 of the penetrating member 25 can have any configuration desired for a particular procedure, for example, the pyramidal trocar configuration shown or a conical distal end (FIG. 15), a threaded distal end (FIG. 16), a multifaceted distal end (i.e., having greater than three facets as shown in FIG. 17), a blunt distal end (FIG. 18), a slanted distal end (FIG. 19) or a hollow needle configuration with fluid flow therethrough (FIG. 20). Additionally, the surface defining the distal end of the penetrating member can be irregular or smooth, continuous or perforated, provided with cutting features or having any combination of the above. If the penetrating member 25 is a hollow needle having a beveled end as shown in FIG. 20 or a curved Toohey-type distal configuration, the proximal edge of the opening at the distal end 94 of the needle is considered the transverse dimensional transition 95 and thus the cannula and/or safety shield distal end is aligned with the distal end of the needle when located adjacent the proximal edge.

Figure 21:
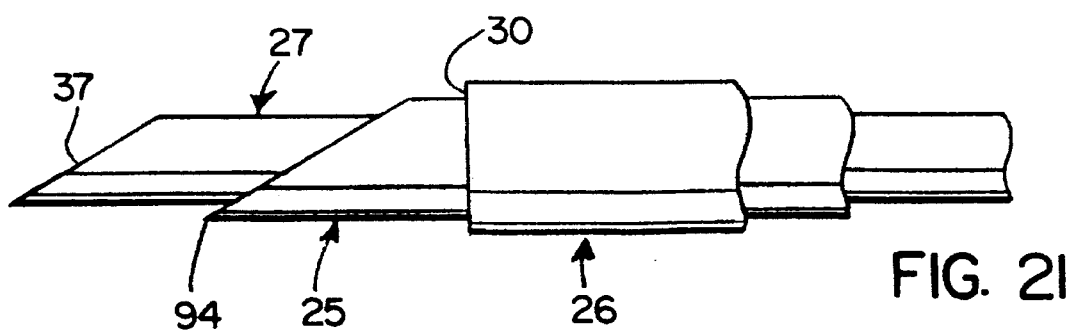
FIG. 21 is a side view of the distal end of a penetrating member configured to accommodate a safety probe.

As mentioned previously, the safety member of the present invention can be a tubular member such as the cannula or a safety shield disposed between the cannula and penetrating member, or in the case of a hollow penetrating member, the safety member can be a probe disposed at least partially within the penetrating member and movable through one or more apertures formed at or near the distal end of the penetrating member. FIG. 21 shows a cannula 26 surrounding a hollow penetrating member 25 with a beveled distal end 94 and a cylindrical safety probe 27 in an extended protruding position to protect the distal end of the penetrating member. The safety probe 27 has a beveled distal end 37 and is preferably movable from the extended position shown to a retracted position where the beveled distal end 37 of the safety probe 27 is flush with the distal end 94 of the penetrating member 25. It will be appreciated that a coaxial extending mechanism can be fitted within the penetrating member to move the safety probe to the extended position or a flange can be carried at the safety probe proximal end and passed through a slot or opening in the penetrating member to be acted on by any of the extending mechanisms previously described. The safety probe distal end can have any configuration to protrude through single or multiple openings formed in the penetrating member distal end and can conform to the distal profile of the penetrating member or present a discontinuous surface.

The rail member can have various configurations to engage the latch and be released by the trigger. Preferably, the rail member will have a configuration to serve as a stop or abutment for the operating member as exemplified herein by a U-shaped rail member.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in applicant's pending applications Ser. Nos. 07/800,507, filed Nov. 27, 1991, 07/805,506, filed Dec. 6, 1991, 07/808,325, filed Dec. 16, 1991, 07/848,838, filed Mar. 10, 1992, 07/868,566 and 07/868,578, filed Apr. 15, 1992, 07/929,338, filed Aug. 14, 1992, 07/845,177, filed Sep. 15, 1992, 07,945,177, filed Sep. 15, 1992, 08/079,586, filed Jun. 22, 1993, 08/195,512, filed Feb. 14, 1994, 08/196,029, filed Feb. 14, 1994, 08/196, 027, filed Feb. 14, 1994, 08/195,178, filed Feb. 14, 1994, 08/237,734, filed May 4, 1994, 08/247,205, filed May 20, 1994, 08/254,007, filed Jun. 3, 1994 and 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in applicant's copending patent application Ser. Nos. 08/279,170 and 08/279,172, filed Jul. 22, 1994, the disclosures of which are incorporated herein by reference.

One or more control buttons, such as the control buttons described in applicant's copending patent application Ser. No. 08/083,220, filed Jun. 24, 1993, the disclosure of which is incorporated herein by reference, can be mounted next to any latch for manually disengaging the latch to prevent locking of the safety member in the retracted position, thereby converting the safety penetrating instrument to a standard safety shielded penetrating instrument without triggered protrusion. In addition, any latch can carry a secondary pawl or protrusion at a distal end for locking the safety member in the extended position and can then be released through the use of a control button as described above.

It will also be appreciated that the safety penetrating instrument of the present invention permits use of strong bias springs to ensure movement of the safety member (whether it be the cannula, a safety shield or probe, or both) to the extended protruding position without increasing the force to penetrate. After penetration of the safety penetrating instrument into the anatomical cavity, the safety member acts as a shock absorber upon inadvertent contact with tissue which contact can be felt by the user and visually determined by movement of the handle. The distal bias for the cannula of the safety penetrating instrument need only be strong enough to allow slight movement of the cannula during penetration such that the force-to-penetrate can be minimized. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

extending means for moving said cannula distally from a retracted position where said cannula distal end is disposed proximally of said penetrating member distal end to an extended position where said cannula distal end protrudes distally from said penetrating member distal end;

means for manually moving said cannula proximally relative to said housing from said extended position to said retracted position;

locking means for locking said cannula in said retracted position to prevent distal movement of said cannula relative to said housing beyond said retracted position while permitting proximal movement of said cannula relative to said housing during penetration of the anatomical cavity wall;

bias means for biasing said cannula distally relative to said housing in said retracted position to permit said cannula to move proximally relative to said housing from said retracted position during penetration of the anatomical cavity wall and distally relative to said housing toward said retracted position upon introduction in the anatomical cavity; and releasing means responsive to movement of said cannula distally toward said retracted position upon introduction in the anatomical cavity for triggering release of said locking means to permit said extending means to move said cannula distally relative to said housing from said retracted position to said extended position.

2. A safety penetrating instrument as recited in claim 1 and further including means at said distal end of said cannula for increasing resistance of said cannula to passage through the anatomical cavity wall to cause said cannula to move proximally from said retracted position against said bias means during penetration of the anatomical cavity wall.

3. A safety penetrating instrument as recited in claim 2 wherein said means for increasing resistance includes a textured surface on said cannula.

4. A safety penetrating instrument as recited in claim 2 wherein said means for increasing resistance includes a formation at said cannula distal end having a configuration to resist passage through the anatomical cavity wall.

5. A safety penetrating instrument as recited in claim 1 wherein said penetrating member distal end extends distally from a transverse dimensional transition in said penetrating member and said cannula distal end is aligned with said transition when in said retracted position.

6. A safety penetrating instrument as recited in claim 1 wherein said penetrating member distal end extends distally from a transverse dimensional transition in said penetrating member and said cannula distal end is located proximally of said transition when in said retracted position.

7. A safety penetrating instrument as recited in claim 1 wherein said penetrating member distal end extends distally from a transverse dimensional transition in said penetrating member and said cannula distal end is located distally of said transition when in said retracted position.

8. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

a safety member disposed within said cannula and having a distal end, said safety member being movable relative to said housing between an extended position where said safety member distal end protrudes distally from said penetrating member distal end and a retracted position where said safety member distal end is disposed proximally of said penetrating member distal end to expose said penetrating member distal end;

extending means for moving said safety member distally relative to said housing from said retracted position to said extended position;

means for manually moving said safety member proximally relative to said housing from said extended position to said retracted position;

locking means for locking said safety member in said retracted position to prevent movement of said safety member to said extended position during penetration of the anatomical cavity wall;

bias means for biasing said cannula distally relative to said housing to permit movement of said cannula proximally relative to said housing during penetration of the anatomical cavity wall and distally relative to said housing upon introduction in the anatomical cavity; and releasing means responsive to movement of said cannula distally upon introduction in the anatomical cavity for triggering release of said locking means to permit said extending means to move said safety member distally relative to said housing from said retracted position to said extended position.

9. A safety penetrating instrument as recited in claim 8 wherein said safety member includes a safety shield.

10. A safety penetrating instrument as recited in claim 9 and further including means at said cannula distal end for increasing resistance of said cannula to passage through the anatomical tissue to cause said cannula to move proximally during penetration of the anatomical cavity wall.

11. A safety penetrating instrument as recited in claim 10 wherein said means for increasing resistance includes a textured surface on said cannula.

12. A safety penetrating instrument as recited in claim 10 wherein said means for increasing resistance includes a formation having a configuration to resist passage through the anatomical cavity wall.

13. A safety penetrating instrument as recited in claim 8 wherein said penetrating member distal end extends distally from a transverse dimensional transition in said penetrating member and said safety member distal end is aligned with said transition when said safety member is in said retracted position.

14. A safety penetrating instrument as recited in claim 13 wherein said bias means urges said cannula distal end into alignment with said safety member distal end when said safety member is in said retracted position.

15. A safety penetrating instrument as recited in claim 13 wherein said cannula distal end is located proximally of said safety member distal end when said safety member is in said retracted position.

16. A safety penetrating instrument as recited in claim 13 wherein said bias means urges said cannula distal end distally of said safety member distal end when said safety member is in said retracted position.

17. A safety penetrating instrument as recited in claim 8 wherein said penetrating member distal end extends distally from a transverse dimensional transition in said penetrating member and said safety member distal end is located proximally of said transition when said safety member is in said retracted position prior to use.

18. A safety penetrating instrument as recited in claim 17 wherein said bias means urges said cannula distal end into alignment with said safety member distal end when said safety member is in said retracted position.

19. A safety penetrating instrument as recited in claim 17 wherein said cannula distal end is located proximally of said safety member distal end when said safety member is in said retracted position.

20. A safety penetrating instrument as recited in claim 17 wherein said bias means urges said cannula distal end distally of said safety member distal end when said safety member is in said retracted position.

21. A safety penetrating instrument for establishing a portal in the wall of an anatomical cavity wall comprising a housing;

an elongate cannula mounted by said housing and having a distal end for positioning in the anatomical cavity and a proximal end for positioning externally of the anatomical cavity;

a penetrating member disposed in said cannula and having a distal end for penetrating the anatomical cavity wall;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula proximally relative to said housing from said cannula extended position to said cannula retracted position;

cannula locking means for locking said cannula in said cannula retracted position to prevent distal movement of said cannula relative to said housing beyond said cannula retracted position while permitting proximal movement of said cannula relative to said housing during penetration of the anatomical cavity wall;

bias means for biasing said cannula distally relative to said housing in said cannula retracted position to permit said cannula to move proximally relative to said housing from said cannula retracted position during penetration of the anatomical cavity wall and distally relative to said housing toward said cannula retracted position upon introduction in the anatomical cavity;

a safety member disposed within said cannula and having a distal end, said safety member being movable relative to said housing between a safety member extended position wherein said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said safety member retracted position during penetration of the anatomical cavity wall; and releasing means responsive to movement of said cannula distally upon introduction in the anatomical cavity for triggering release of said cannula and safety member locking means to permit said cannula and safety member extending means to move said cannula and safety member distally relative to said housing from their respective retracted positions to their respective extended positions.

22. A safety penetrating instrument as recited in claim 21 wherein said safety member includes a safety shield disposed between said cannula and said penetrating member.

23. A safety penetrating instrument as recited in claim 21 and further including means at said distal end of said cannula for increasing resistance of said cannula to passage through the anatomical cavity wall to cause said cannula to move proximally against said bias means during penetration of the anatomical cavity wall.

24. A safety penetrating instrument as recited in claim 21 wherein said safety member has a proximal end and further comprising housing means for mounting said cannula proximal end and said safety member proximal end, said penetrating member passing through said housing means whereby said penetrating member can be withdrawn from said cannula leaving said safety member within said cannula.

25. A safety penetrating instrument as recited in claim 21 wherein said penetrating member extends distally from a proximal end, said safety member extends distally from a proximal end and further including hub means for mounting said penetrating member proximal end and said safety member proximal end whereby said penetrating member and said safety member can be withdrawn from said cannula together by grasping said hub means.

26. A safety penetrating instrument as recited in claim 21 wherein said penetrating member distal end extends distally from a transverse dimensional transition in said penetrating member and said safety member distal end is aligned with said transition when said safety member is in said retracted position.

27. A safety penetrating instrument as recited in claim 26 wherein said bias means urges said cannula distal end into alignment with said safety member distal end when said safety member is in said retracted position.

28. A safety penetrating instrument as recited in claim 26 wherein said cannula distal end is located proximally of said safety member distal end when said safety member is in said retracted position.

29. A safety penetrating instrument as recited in claim 26 wherein said bias means urges said cannula distal end distally of said safety member distal end when said safety member is in said retracted position.

30. A safety penetrating instrument as recited in claim 21 wherein said penetrating member distal end extends distally from a transverse dimensional transition in said penetrating member and said safety member distal end is located proximally of said transition when said safety member is in said retracted position.

31. A safety penetrating instrument as recited in claim 30 wherein said bias means urges said cannula distal end into alignment with said safety member distal end when said safety member is in said retracted position.

32. A safety penetrating instrument as recited in claim 30 wherein said cannula distal end is located proximally of said safety member distal end when said safety member is in said retracted position.

33. A safety penetrating instrument as recited in claim 30 wherein said bias means urges said cannula distal end distally of said safety member distal end when said safety member is in said retracted position.

* * * * *